United States Patent [19]

Chang

[11] Patent Number: 5,670,626

[45] Date of Patent: Sep. 23, 1997

[54] ALLERGEN-SPECIFIC HUMAN IGA MONOCLONAL ANTIBODIES FOR MUCOSAL ADMINISTRATION

[75] Inventor: Tse Wen Chang, Houston, Tex.

[73] Assignee: Tanox Biosystems, Inc., Houston, Tex.

[21] Appl. No.: 263,258

[22] Filed: Jun. 21, 1994

Related U.S. Application Data

[63] Continuation-in-part of Ser. No. 994,126, Dec. 21, 1992, abandoned.

[51] Int. Cl.⁶ .............. C07K 16/14; C07K 16/16; C07K 16/18
[52] U.S. Cl. .................. 530/388.5; 530/388.85
[58] Field of Search .................. 530/388.5, 388.85

[56] References Cited

U.S. PATENT DOCUMENTS

| | | | |
|---|---|---|---|
| 4,226,853 | 10/1980 | Marsh | 424/91 |
| 4,474,893 | 10/1984 | Reading | 436/547 |
| 4,722,899 | 2/1988 | Hamaoka et al. | 435/172.2 |
| 4,861,579 | 8/1989 | Meyer et al. | 424/1.1 |
| 5,026,545 | 6/1991 | Saint-Remy et al. | 424/85.8 |
| 5,169,627 | 12/1992 | Cunningham-Rundles . | |

FOREIGN PATENT DOCUMENTS

| | | |
|---|---|---|
| 0498124 | 12/1991 | European Pat. Off. . |
| WO9116061 | 10/1991 | WIPO . |
| WO9311160 | 6/1993 | WIPO . |
| WO9317703 | 9/1993 | WIPO . |

OTHER PUBLICATIONS

Weltzin R. et al. Binding and Transepithelial Transport of Immunoglobulins by Intestinal M Cells: Demonstration Using Monoclonal IgA Antibodies Against Enteric Viral Proteins. The Journal of Cell Biology, vol. 108, No. 5, May 1989.

Mazanec B. et al. Immunoglobulin A Monoclonal Antibodies Protect Against Sendai Virus. Journal of Virology, vol. 61, No. 8, Aug. 1987.

Saint-Remy J. et al. Human Immune Response to Allergens of House Dust Mite, Dermatophagoides Pteronyssinus. Allergy, vol. 43, No. 5, Jul. 1988.

Chua, K.Y., "Sequence Analysis of cDNA Coding for a Major House Dust Mite Allergen", J. Exp. Med. 167:175–182 (1988).

Hamilton, RG, "Measurement of Allergen–Specific Immunoglobulin G Antibody", Allergic Diseases, Chapter 102:702–708, 1992.

Hamilton, RG, "Measurement of Total Serum Immunoglobulin E and Allergen–Specific Immunoglobulin E Antibody", Allergic Diseases, Chapter 101:689–701, 1992.

de Groot, H, "Affinity purification of a major and a minor allergen from dog extract: Serologic activity of affinity–purified Can fI and of Can fI–depleted extract", J. Allergy Clin. Immunol., 87:1056–1065 (1991).

Lake, FR, "House dust mite–derived amylase: Allergenicity and physiochemical characterization", J. Allergy Clin. Immunol. 87:1035–1042 (1991).

Lau–Schadendorf, S, "Short–term effect of solidified benzyl benzoate on mite–allergen concentrations in house dust", J. Allergy Clin. Immunol. 87:41–47 (Jan. 1991).

Morgenstern, JP, "Amino acid sequence of Fel dI, the major allergen of the domestic cat: Protein sequence analysis and cDNA cloning", Proc. Natl. Acad. Sci. USA 88:9690–9694 (1991).

Bond, JF, "Multiple Amb a I Allergens demonstrate specific reactivity with IgE and T cells from ragweed–allergic patients", J. of Immunol. 146:3380–3385, 1991.

Baraniuk, JN, "Pollen grain column chromatography: quantitation and biochemical analysis of ragweed–pollen solutes", J. Allergy Clin. Immunol. 81:1126–1134, 1988.

Ray, M.C., et al., *J. Immunology*, vol. 131, No. 3, pp. 1096–1102, 1983, Abstract Only.

Seaver, Genetic Engineering News, pp. 10 and 21 (1994).

Burton, Techniques In Molecular Biology, vol. 2, Walker et al. (eds), Macmillan Publishing Company, New York pp. 55–81 (1987).

Sevier et al., Clinical Chemistry, vol. 27, No. 11, pp. 1797–1806 (1981).

*Primary Examiner*—Toni R. Scheiner
*Attorney, Agent, or Firm*—Eric P. Mirabel

[57] ABSTRACT

Disclosed are pharmaceutical preparations containing human monoclonal IgA antibodies specific for major allergenic proteins found in ragweed, house dust mites, and cat and dog dander. Also disclosed are constructs comprising physiological compatible polymer backbones or microbeads and a plurality of covalently conjugated allergen-specific binding molecules. Such binding molecules are IgG or IgA, or their F(ab')₂, Fab, or Fv fragments, specific to the major allergenic proteins mentioned above. Also disclosed are methods for treating a patient with allergic rhinitis, asthma, or conjunctivitis by applying a pharmaceutical preparation containing the antibodies specific for the allergenic molecules, to which the patient is sensitized, to the patient's affected mucosal tissues, such as the nasal linings, the respiratory tract, or the eyes.

2 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: Linear ( x i ) SEQUENCE DESCRIPTION: SEQ ID NO:1:

TGCGGCCGCT GCTGAGGGAG TAGA 24

( 2 ) INFORMATION FOR SEQ ID NO:2:

( i ) SEQUENCE CHARACTERISTICS:
   ( A ) LENGTH: 16 nucleotides
   ( B ) TYPE: nucleic acid
   ( C ) STRANDEDNESS: single
   ( D ) TOPOLOGY: Linear ( x i ) SEQUENCE DESCRIPTION: SEQ ID NO:2:

AATTCGAACC CCTTCG 16

( 2 ) INFORMATION FOR SEQ ID NO:3:

( i ) SEQUENCE CHARACTERISTICS:
   ( A ) LENGTH: 12 nucleotides
   ( B ) TYPE: nucleic acid
   ( C ) STRANDEDNESS: single
   ( D ) TOPOLOGY: Linear ( x i ) SEQUENCE DESCRIPTION: SEQ ID NO:3:

CGAAGGGGTT CG 12

( 2 ) INFORMATION FOR SEQ ID NO:4:

( i ) SEQUENCE CHARACTERISTICS:
   ( A ) LENGTH: 20 nucleotides
   ( B ) TYPE: nucleic acid
   ( C ) STRANDEDNESS: single
   ( D ) TOPOLOGY: Linear ( x i ) SEQUENCE DESCRIPTION: SEQ ID NO:4:

AGGTGTGCAC GCCGCTGGTC 20

( 2 ) INFORMATION FOR SEQ ID NO:5:

( i ) SEQUENCE CHARACTERISTICS:
   ( A ) LENGTH: 25 nucleotides
   ( B ) TYPE: nucleic acid
   ( C ) STRANDEDNESS: single
   ( D ) TOPOLOGY: Linear ( x i ) SEQUENCE DESCRIPTION: SEQ ID NO:5:

CAAGCTTCCA CGACACCGTC ACCGG 25

( 2 ) INFORMATION FOR SEQ ID NO:6:

( i ) SEQUENCE CHARACTERISTICS:
   ( A ) LENGTH: 30 nucleotides
   ( B ) TYPE: nucleic acid
   ( C ) STRANDEDNESS: single
   ( D ) TOPOLOGY: Linear ( x i ) SEQUENCE DESCRIPTION: SEQ ID NO:6:

GCCCTGGGCT GCCTGGTCAA GGACTACTTC 30

ALLERGEN-SPECIFIC HUMAN IGA MONOCLONAL ANTIBODIES FOR MUCOSAL ADMINISTRATION

This is a continuation-in-part of application Ser. No. 07/994,126 filed on Dec. 21, 1992, Abandoned.

FIELD OF THE INVENTION

The invention relates to the treatment of IgE-mediated allergies, such as allergic rhinitis, allergic asthma, and allergic conjunctivitis by administering to the mucosal surfaces of nasal linings, airway, and eyes a solution or a suspension that contains human monoclonal IgA antibodies specific for the allergens to which the treated patient is sensitized.

BACKGROUND OF THE INVENTION

Immunoglobulin E (IgE) is mainly responsible for causing type-1 hypersensitivities, which manifest some of the most common human diseases, such as allergic rhinitis, allergic asthma, and allergic conjunctivitis. In patients with IgE-mediated allergies, allergen-specific IgE is synthesized. IgE circulates in the blood and binds to high-affinity IgE.Fc receptors (FcεRI) on basophils in the circulation and on mast cells in various tissues. In an allergic response, the allergens enter the body of a patient through inhalation, ingestion, or through the skin. The allergen molecules bind to the binding sites (Fab) of IgE on the surfaces of mast cells and basophils, aggregate the underlying FcεRI, and hence trigger the release of histamine and other pharmacological mediators, causing the manifestation of various disease symptoms.

Among the tissues that are most susceptible to local IgE-mediated allergic reactions are the nasal linings (in patients with allergic rhinitis), the mucosal linings of bronchial tracts (in patients with allergic conjunctivitis). The reason for this local sensitivity is that the allergens enter the respiratory tract through inhalation and get trapped on the mucosal surfaces of the nasal linings and bronchial tracts of the respiratory airway. The eyes and ears are also very sensitive sites and become inflammatory. Airborne allergens come to contact with the moist surfaces of the eyes and ears and are retained by the mucous tissues. The mast cells are densely populated along the mucosal tissues that are exposed to the exterior environment. The allergens that are taken up by the mucosal epithelial cells and transported across the cells to the interstitial spaces bind to the IgE on these mast cells before entering the circulation.

Although the synthesis of allergen-specific IgE seems to be the dominant factor in the development of IgE-mediated sensitivities, the amount or the concentration of allergen-IgE is not the only factor in deciding the extent of a patient's sensitivity. Patients and persons who are exposed to but not sensitized to an allergen are known to produce IgG specific to the allergen. It is believed that these allergen-specific IgG serve as protective, blocking antibodies. People with IgA deficiency are more prone to develop IgE-mediated allergies, suggesting that IgA secreted to the mucosal surfaces of the respiratory tract can neutralize or block the trapped allergen particles or molecules, reducing their entry into the tissue. In the widely used desensitization immunotherapy treatment, patients are immunized with small amounts of allergens over a course of several months to several years. While this therapy is effective in alleviating symptoms in about half of the allergic patients, it is not well understood by what mechanisms it works in those patients. One favorable explanation is that the treatment induces IgG blocking antibodies, because elevated levels of these antibodies can be detected in the treated patients.

The therapeutical principles and treatment modalities in the medical practice of allergy have not substantially changed over the past seventy or eighty years. Desensitization immunotherapy is the main therapy for the more severe patients with allergic rhinitis. Immunosuppressive drugs, such as steroids, for suppressing immune activities, and bronchial dilators, such as α-albuterol, for relieving asthmatic symptoms, have been the main treatment modality for patients with allergic asthma. The medical advances have been very much limited to finer classification of the allergenic substances, finer diagnostic methods for determining a patient's profile of sensitive allergens, and a better controlled and broader library of allergen extracts for immunotherapy. On the research side, a lot of progress has been made in the identification and the isolation of major allergenic molecular components in allergenic substances. For example, the chief protein components in ragweed (the most important allergen in causing hay fever in the fall season), in house dust mites (the most important allergen in causing allergic asthma), and in cat and dog dander and saliva. The genes of several major allergens have been cloned.

Thanks to the development of methodologies for immortalizing human B lymphocytes using cell fusion or transformation with Epstein-Barr virus (EBV), it is possible to identify human monoclonal antibodies with antigen specificity of interest. The more recent development of methodologies to construct recombinant phage incorporating human $V_H$ and $V_L$ libraries, to express the combinatorial $V_H/V_L$, and to screen the expressed antibody fragments for antigen specificity have added another powerful tool in the identification of antibody species of interest. In addition, the improvement in gene transfection and expression of antibody genes in myeloma or other cell lines have enabled the production of human monoclonal antibodies in large quantities.

SUMMARY OF THE INVENTION

The invention relates to the treatment of IgE-mediated allergic diseases, such as allergic rhinitis, allergic (extrinsic) asthma, and allergic conjunctivitis, by employing antibodies to inhibit the entry of allergenic molecules into mucosal tissues ("immune exclusion"). The invention theorizes that as the particles containing the allergenic molecules are in contact with the mucous fluids on the mucosal surface, the allergenic molecules are released from the particles and are accessible for binding by allergen-specific antibodies. The binding by antibodies inhibit the allergenic molecules to be taken up by the mucosal epithelial cells. IgA antibodies are chosen because they are more resistant to proteolytic cleavage by proteases in the mucosal fluids.

The invention relates to the identification of monoclonal antibodies or their $V_H$ and $V_L$ fragments specific for major allergenic proteins or other molecular components in allergenic substances. These proteins include Amb a I, the dominant allergen in short ragweed (*Ambrosia elator*), Der p I and Der f I, the major allergens from house dust mite species (*Dermatophagoides pteronyssinus* and *Dermatophagoides farinae*), Fel d I, the major allergen from the saliva of house cats (*Felis domesticus*), and Can fI, the major allergen from the dander of domestic dogs (*Canis familiaris*). The B cells expressing antibodies of such antigen specificities are obtained from patients who have natural sensitivities to the allergens or who have been immunized with the allergens in desensitization immunotherapy. The B cells from these donors are immortalized by fusion with myeloma cells, such as NSO or SP2/0 cells, or transformed with EBV. The antibodies secreted by these immortalized cell lines are screened by ELISA or comparable immunochemical assays for specific reactivity with the allergens of interest. The $V_H$ and $V_L$ of antibody fragments may also be identified with the combinatorial $V_H/V_L$ library expression and screening methodologies.

The genomic DNA fragment containing the segment encoding $V_H$ domain of an antibody of a desired specificity is linked to the genomic DNA fragment containing segments encoding the constant domains (CH1, CH2 and CH3) of human α chain. The genomic DNA fragment of the $V_L$ is linked to the genomic DNA fragment of human or κ or λ light chain. The recombinant DNA species in their appropriate plasmids were then used to transfect cells of a nonproducer myeloma cell line, such as NSO or SP2/0. The procedures for the construction of the composite DNA fragments, the transfection of the recipient cell line with the DNA, and the screening of the transfectants for production of monoclonal IgA antibodies specific for the allergen/antigen are similar to those procedures used for preparing transfectoma cell lines producing chimeric antibodies.

In a different embodiment of the invention, the allergen-specific IgA or IgG, or the antigen-binding fragments of these antibodies, such as $F(ab')_2$, Fab, or Fv, are conjugated to polymer backbones or microbeads. These polymers are not allergenic and are harmless to patients, and with proper modification can provide active sites for the conjugation of many antibody molecules. Examples of these polymers include dextran, agarose, and cellulose. The microbeads include those made from the cross-linking of these polymers. The polymerized conjugates may have the advantage that they are less likely to be absorbed by the mucosal epithelial cells and probably more likely to be cleared along with the mucous secretion.

The allergen-specific IgA or IgG, or their related constructs in a physiological solution or suspension are to be applied to the mucosal tissues of patients who are allergic to the allergen. The clinical benefit is that the antibodies can bind to the allergenic protein (or other molecules to be targeted) that is released from the inhaled particles. TMs binding inhibits the allergen to be taken up by the mucosal epithelial cells and hence alleviate the development of allergic symptoms. In a preferred embodiment of the invention, the allergen-specific human monoclonal IgA antibodies are prepared in a physiological buffer for applying by dropping to the noses, eyes, or ears at the amounts of 1–2 drops per nostril, eye, or ear. The concentration of the IgA in the solution is in the range of 20 to 1000 µg per ml, which is equal to 1 to 50 µg of antibody per drop. The IgA may also be prepared in a solution for administration with a metered dose inhaler for reaching mucosal tissues at lower parts of the respiratory tract. The IgA concentrations are in the same range. The IgA antibody may be applied every 2 to 4 hours. It may be applied with a decongestant medication.

The allergen-specific IgA and IgG, and their various conjugates with polymers and microbeads also have attractive applications in the manufacturing of allergenic substances for diagnostic uses and for desensitization immunotherapy. The allergen-specific antibodies can be incorporated into an affinity column for purifying the specific allergens in the crude extracts of allergenic substances, such as ragweed, house dusts, and cat and dog dander. The purified allergens are preferred for use in the standardization of allergen extracts. The purified altergens are better antigens than the crude extracts for diagnostic uses and for immunotherapy.

The purified allergen-specific IgA and IgG can be used as standards in the diagnostic assays for measuring allergen-specific antibodies in the patients receiving immunotherapy.

The IgG and IgA allergen-specific human monoclonal antibodies of the invention can also be used in standard assay formats, such as an ELISA for detection or quantitation of allergens in a sample. In an example of this format, the antibodies can be bound to a plate, and the sample containing the allergen passed over the plate. The allergens which are bound are detected by adding a second, different antibody which binds to the allergens and which is linked to a label. When the label is activated by addition of a suitable enzyme, the presence of color indicates the presence of allergen, and the degree of color can indicate the quantity of allergen present.

DETAILED DESCRIPTION OF THE INVENTION (A) Minute quantities of allergens come in contact with a patient Although IgE can cause annoying, discomforting, and sometimes, severe and death-threatening symptoms in the affected individuals, it exists in the body of a person in relatively minute quantities. Statistically the levels of IgE in serum are higher in atopic than in normal individuals. The total amount of IgE in the body is estimated to be less than 1 mg in most individuals. Thus the immune mechanism mediated by IgE and the sensitization of mast cells and basophils is an extremely sensitive biological system. It has also been appreciated that it requires very minute amounts of antigens/allergens to induce serious allergic reactions. For an individual highly sensitive to bee venom, the sting of a bee can cause an anaphylactic shock or even death. The responsible allergenic proteins are only minor chemical components in this Hymenoptera venom. It has been analyzed that small numbers of pollen particles or animal dander particles are capable of triggering the allergic reactions in the nasal linings and in the airway of sensitized individuals.

Under most situations, the altergens enter the body of a person not in their pure chemical forms. The responsible allergenic molecules in the pollen particles, house dust mites, and animal dander, that are breathed in, are relatively minor components of the whole particles. For example, the content of the main allergic protein, antigen $P_1$, of dust mite *Dermatophagoides pteronyssinus* (Der p I) in a household highly infested by the mites account for about 10–20 µg per g of dusts. Lau-Schadendorf,S. et al., *J. Allergy Clin. Immunol.* 87: 41–47 (1991). The protein is a cysteine protease contained in the fecal excretion of the mites. These analyses suggest that for a therapeutical approach that employs specific antibodies to molecularly avoid or block the entry of allergenic molecules into the mucosal tissue, only small quantities of these antibodies are required.

(B) Allergenic molecules are released from particles in mucus before being taken up Allergenic molecules should be substantially accessible by the allergen-specific antibodies so that their entry to the mucosal tissue is inhibited. The allergenic proteins are soluble in aqueous medium and should be readily soluble in the mucous fluids once they are released from the particles. The mucus contains a host of hydrolytic enzymes that should aid in digesting and loosening the contents of the particles. In any event, one can assume that the mucosal epithelium does not take up the whole pollen or mite particles and that only the released, soluble allergenic molecules are pertinent in causing the allergic reactions. The hypothesis that pollen particles or house dust particles release the crucial allergenic proteins into the mucous fluids is testable. A sample of collected house dusts can be incubated with nasal mucous secretion in vitro for varying lengths of time (1 minute to 30 minutes), the mixture is then centrifuged to pellet particles. The content of Der p I protein in the supernatant is then measured by a standard immunochemical assay for Der p I (see below).

(C) Major allergenic proteins have been identified

In the medical practice of allergy the allergenic substances being employed in diagnosis and immunotherapy have been almost entirely extracts of allergenic substances, such as grass or tree pollens, house dusts, cat and dog dander. Because the crude nature of the extracts, the International Union of Immunological Societies of the World Health Organization set up Allergen Standardization Subcommittee to oversee the standards of production, packaging, and preliminary testing of the allergens. For a number of allergenic substances the standard tests are assays that quantify the major allergenic proteins in the extracts.

Over the past several years, increasing efforts have been made to identify and purify the major allergenic proteins from increasing numbers of allergenic substances. For example, the major allergen Can f I (antigen 13) was purified from dog dander. De Groot, H., et al., *J. Allergy Clin. Immunol.* 87: 1056–1065 (1991). Several academic laboratories have been able to provide immunochemical assays for allergen-specific IgE and IgG using purified allergen proteins as the antigens in these assays. Hamilton, R. G. and Adkinson, Jr., N. F. in *Manual of Clinical Laboratory Immunology*, eds. Rose, N. R. et al., pp. 689–701, 4th ed., American Society of Microbiology, Washington, D.C. (1992); Hamilton, R. G. and Adkinson, Jr., N. F. ibid., pp. 702–708. These purified allergenic proteins and the establishment of the immunochemical assays for human allergen-specific IgG are useful for the identification of B cell clones and monoclonal antibodies specific for the allergens (see below).

More recently the genes encoding several major allergenic proteins have been cloned. For example, the cDNA for the major mite antigen, Der p I. Chua, K. Y. et al., *J. Exp. Med.* 167: 175–182 (1988); the cDNA for the major allergen in cat saliva, Fel d I. Morgenstern, J. P. et al., *Proc. Natl. Acad. Sci. U.S.A.* 88:9690–9694 (1991). The cloning of the genes of these proteins enables their expression and the production of the recombinant proteins.

(D) Allergen-specific IgE and IgG in patients

Patients who are allergic to a protein or other molecular substances make IgE against the molecules. The levels of these IgE are usually low. For the purpose of the of the therapeutical approach of the present invention, it may seem desirable to isolate the B cell clones expressing the IgE specific for the allergens. The $V_H$ and $V_L$ gene segments can be used for the construction of the IgA monoclonal antibodies. In consideration of the low levels of allergen-specific IgE in patients, it is logical to isolate B cell clones expressing allergen-specific IgG. It is known that patients who are sensitized to an allergenic protein synthesizes not only allergen-specific IgE but also allergen-specific IgG. In fact, the levels of the allergen-specific IgG are much higher than those of the allergen-specific IgE. Ishizaka, K. in *Allergy: Principles and Practice*, eds. Middleton. Jr., E., et al., pp. 52–70, 3rd ed., The C. V. Mosby Co., St. Louis (1988). In patients who have received desensitization immunotherapy by the repetitious immunization with the allergens, the allergen-specific IgG levels are much higher than those in unimmunized patients. Hamilton, R. G. and Adkinson, Jr., N. F. in *Manual of Clinical Laboratory Immunology*, eds. Rose, N. R. et al., pp. 702–708, 4th ed., American Society of Microbiology, Washington, D.C. (1992). These immunized patients will provide the best source of lymphocytes for the isolation of allergen-specific B cell clones or antibody genes. In Example 1, the procedure to select donors for the source of allergen-specific B lymphocytes is described.

(E) Isolating allergen-specific B cell clones and antibody genes

The patients who have sensitivity to an allergen and who have been or are being immunized with the allergen can be identified by the allergist physicians treating them. The extent of improvement resulting from the immunization can be used as an indicator that the patient has made good immune response to the allergen/immunogen. The levels of allergen-specific IgG in those patients can be further evaluated by the assays for allergen-specific IgG. Hamilton, R. G. and Adkinson, Jr., N. F. in *Manual of Clinical Laboratory Immunology*, eds. Rose, N. R. et al., pp. 702–708, 4th ed., American Society of Microbiology, Washington, D.C. (1992). The peripheral blood from these patients can be used as the source for allergen-specific B cells, from which the genes for the $V_H$ and the $V_L$ of the allergen-specific antibodies are to be isolated.

Established methods for immortalizing human B cells by EBV transformation or by fusion with myeloma cells (such as NSO cells), or by the combination of these procedures can be used for the present purpose. The EBV transformation procedure for the establishment of B cell clones is recently summarized in step-by-step format by Tosato, G. in *Current Protocols in Immunology*, eds. Coligan, J. E., et al., §7.22.1, John Wiley and Sons, New York (1991). Similarly, the step-by-step procedure for preparing hybridomas, which applies to murine or human lymphocytes, is described by Yokoyama, W. M. ibid. §2.5. These procedures also describe the methods for screening the immortalized B cell clones for the secretion of antibodies with the desired antigen specificity, the sequential subcloning of the B cell clones, and the production of the antibodies. In Example 2, the establishment of enzyme-linked immunosorbent assays (ELISAs) for the detection and measurement of allergen-specific IgG and IgA is described.

An alternative method for the identification and isolation of the genes encoding the allergen-specific antibodies is to employ the "$V_H/V_L$ combinatorial library" methodology. The B cells from the peripheral blood of donors are prepared. The individual $V_H$ and $V_L$ libraries are prepared by polymerase chain reaction (PCR) techniques using degenerate oligonucleotide primers covering the 5' ends of the V regions. The $V_H$ and $V_L$ fragments are then incorporated into one expression vector to be coexpressed to form antibody binding domains. Several expression systems, which have impacts on the screening procedures have been developed. A method that expresses the combined $V_H/V_L$ library in bacteriophage λ vector and presents them in the form of Fab fragments in the lysates of *E. coli* colonies (for subsequent immunochemical screening procedures) was described in details by Barbas, C. F. and Learner, R. A. *Methods: Companion Methods Enzymol.* 2: 119–124 (1991). A method which expresses the $V_H/V_L$ on the surface of filamentous phage fd, which can be isolated with antigen-coupled affinity matrices, was described by McCafferty J. et al., *Nature* 348: 552–554 (1990).

(F) Transfectomas secreting allergen-specific IgA monoclonal antibodies

For achieving the biological effects of excluding immunologically the inhaled or contacted allergens, both IgA and IgG specific for the allergens will function well. However, since IgA is the dominant physiological class functioning at the mucosal surfaces, the preferred allergen-specific antibodies for mucosal applications is IgA. The methods for cloning the restriction enzyme genomic DNA fragments containing $V_H$ and of $V_L$ of allergen-specific IgG antibodies, linking those fragments to the genomic DNA segments of human α and κ (or λ), the transfection of the DNA onto nonproducer myeloma cells, such as NSO or SF2/0 cells, the screening of the transfectants for the secretion of allergen-specific IgA, the sequential cloning for the selection of stable secretors, are in fact the same as those for preparing transfectomas secreting chimeric antibodies which have been described by various investigators in details. Morrison, S. L. et al., *Proc. Natl. Acad. Sci. U.S.A.* 81: 6851–6855 (1984); Liou, R.-S. et al., *J. Immunol.* 143: 3967–3957 (1989).

IgA exists in monomeric and dimeric forms. The circulating IgA is mostly monomeric, whereas the IgA secreted to the mucus or other external fluids is mostly dimeric. The dimeric form has an extra J chain (15,000 daltons) and a secretory component (70,000 daltons), both of which are linked covalently to the α chains of the IgA molecule. The J chain is produced by the same cells that produce the IgA and form the linkage between the two monomeric IgA molecules. The secretory component is synthesized by epithelial cells and is linked to the Fc of the IgA-J chain dimer as it passes through the epithelial cells of the mucosa. Since the dimeric IgA is more stable than the monomeric IgA in the mucous fluids, it is desirable to synthesize dimeric IgA for the present application. To achieve this, the myeloma cell recipient must also be transfected with the gene encoding the J chain, along with the genes for the recombinant α and κ (or λ) chains.

(G) Various constructs of allergen-specific antibodies

The monomeric or dimeric human monoclonal IgA antibodies are probably the most native and the most acceptable antibody molecules that can be introduced to the mucosal surfaces artificially. These molecules are expected to achieve the "immune exclusion" function to prevent the allergenic molecules from entering the mucosal tissue. The immune system has so evolved that the complexes formed by the foreign allergenic molecules and the IgA will not be taken up by the mucosal epithelial cells. The immune complexes on the nasal linings will be excreted as the mucous excretion is expelled externally through the nostrils. The immune complexes and other inhaled particles on the mucosal surfaces of the tracheal and bronchial airways will be expelled into the mouth. The mucus that enters the mouth will be mixed with the saliva, swallowed, and digested by the gastrointestinal tract.

In order to achieve better effects in adsorbing and clearing allergenic molecules from the mucous fluids on the mucosal surfaces and preventing any uptake of the complexed allergen by the mucosal epithelial cells, the allergen-specific IgA or its antigen-binding sites, such as F(ab')$_2$, Fab, or Fv, can be conjugated to polymer backbones or microbeads. For these constructs, allergen-specific IgG and its fragments should also be applicable. The polymers include dextran, agarose, cellulose, and other polymeric substances that are known to be inert, non-allergic, and non-immunogenic. After chemical modification to generate active sites, the a polymer backbone can provide sites for the coupling of a large number of antibody molecules. The microbeads are preferred to be in the range of 0.1–10 μm in diameter and are made of the polymers mentioned above. The suspensions of these microbeads are homogeneous with gentle shaking and hence are suitable for application to the affected mucosal tissues.

(H) Application of allergen-specific antibodies to mucosal surfaces

The modes of application for the allergen-specific IgA monoclonal antibodies will depend on several factors. For determining whether an allergen-specific IgA preparation is suitable for a patient, he (she) needs to be diagnosed for whether the particular allergen is a major allergenic molecule for him (her). If a patient is sensitive to several allergenic molecules, a preparation containing multiple IgA monoclonal antibodies each specific to the allergens may be used.

As discussed in section A, the amounts of allergens entering the mucosal surfaces of a person in most cases are very small. On the other hand, the mucous secretions are being excreted by the mucosal tissues constantly. These suggest that the solution or suspension containing allergen-specific IgA should be applied in small quantities but at frequent intervals. It is estimated that in each individual application to the nasal linings, an eye, or an ear, amounts of 1–50 μg of IgA per nostril, eye, or ear will be sufficient. Depending on the rates of secretion from the nose and from the eyes, the IgA preparation may be applied at a frequency of every two to every six hours. The frequency of application can be reduced with the concurrent use of a decongestant. Because the areas of mucosal surfaces involved in allergic asthma are much larger, more IgA will need to be applied to these surfaces.

The IgA preparation can be applied to the nasal linings, the eye, and the ear with a dropper, which delivers 1–2 drops of the solution to a nostril, an eye or an ear. The concentration of the IgA is in the range of 20 to 1000 μg/ml. The solution can be packaged in 2–5 ml vials and stored in the refrigerator. Once opened, the vial should be used in a week. The solution or suspension containing the allergen-specific IgA at about the same concentrations can be administered to the lower parts of the airway using a metered dose inhaler.

(I) Applications of allergen-specific antibodies in the manufacturing of allergens The allergen-specific IgA and IgG, and their various conjugates with polymers and microbeads also have attractive applications in the manufacturing of pure and safe allergenic substances, which are desirable for use in various diagnostic assays and for use in desensitization immunotherapy. The allergen-specific antibodies can be incorporated into an affinity column for purifying the responsible, specific allergens from the crude extracts of allergenic substances, such as ragweeds, grass and tree pollens, house dusts, and cat and dog dander. The purified allergens are preferred for use in the standardization of allergen extracts. The purified allergens are better antigens than the crude extracts for diagnostic assays and for desensitization immunotherapy. The purified allergen-specific IgA and IgG can be used as standards in the diagnostic assays for measuring allergen-specific antibodies in the patients receiving immunotherapy. These assays are useful in monitoring the efficacy of the immunotherapy.

EXAMPLE 1

Selection of blood donors producing IgG specific for Der p I.

Patients who had a high sensitivity to house dust mites and who have received or are receiving desensitization immunotherapy with mite extract will be identified in the allergy clinic, Allergy Asthma Immunology Associates of Texas in Houston, Tex., directed by Dr. Thomas R. Woehler. A protocol for performing studies on patients' blood samples has been approved by the institutional review board overseeing that clinic. The sera from patients will be tested for containing IgG specific for Der p I in an immunology clinical laboratory, Reference Laboratory for Dermatology, Allergy, and Clinical Immunology in the Johns Hopkins University School of Medicine (Baltimore, Md.), which runs Der p I-specific IgG assay routinely. The sera are also assayed for Der p I-specific IgG using the ELISA described in Example 2 below. The patients with high serum titers of Der p I-specific IgG will be recruited as the donors of blood for the isolation of the antigen-specific B cell clones.

EXAMPLE 2

Establishment of ELISA for Der p I-specific IgG and IgA

The cDNA for Der p I is cloned using a routine PCR method from a sample of house mites purchased from Commonwealth Serum Laboratories, Parkville, Australia. The sequence of the cDNA has been published. Chua, K. Y. et al. *J. Exp. Med.* 167:175–182 (1988). The sequences of the oligonucleotide primers for PCR can be readily designed from the available cDNA sequence. The cDNA can then be expressed in abundant quantities in one of several commercially available systems. A preferred expression system is one that uses the expression vector derived from nuclear polyhedron protein gene of the insect virus baculovirus (*Autographa californica*). The virus can be grown in the insect cells, sf9 cells, from *Sprodoptera frugiperda*. Luckow, V. A. and Summers, M. D. *Virology* 167: 31 (1989). This expression system has been packaged into a convenient kit (designated "Max Bac Baculovirus Express System") and is sold by Invitrogen (San Diego, Calif.). An adequate quantity of the Der p I will be prepared. This purified protein will be used as the solid-phase antigen for the ELISA to detect and assay human IgG or IgA in culture supernatants of immortalized B cell clones or transfectomas. A preferred format for these ELISA is to employ biotin-labeled goat IgG anti-human IgG and goat IgG anti-human IgA, and horseradish peroxidase-conjugated avidin. Harlow,E. and Lane, D. *Antibodies: A Laboratory Manual.* pp. 553–612. Cold Spring Harbor Laboratory (1988). The ELISA may also be used to quantitate Der p I-specific IgG in human sera.

EXAMPLE

Making Human IgG and IgA Monoclonal Antibodies to Amb a I

Purified Amb a I.

Amb a I was purified from defatted short ragweed pollen by Greer Laboratories (Lenoir, N. C.) to greater than 95% purity according to a published procedures (J. R. Orson and D. G. Klapper, *J. Immunol.* 136: 2109 (1986). This preparation showed a single protein band of approximately 40 kD on SDS-PAGE, and was characterized by ELISA using rabbit anti-Amba I antiserum.

Establishment of Cell Lines From Patient PBLs.

Patients who had been receiving desensitization immunotherapy with ragweed extract and had shown improvement of symptoms were identified at Allergy Asthma Immunology Associates of Texas (Houston, Tex.). Ficoll hypaque-isolated PBLs were first immortalized by transformation with EBV, followed by fusion with the mouse myeloma P3×63Ag8.653 cells in the presence of PEG 1000. These cells were plated into 96 well microtiter plates in Iscove's modified DMEM (GIBCO, Grand Island, N.Y.) containing 5% FCS, hypoxanthine (Sigma) at $1 \times 10^4 M$, aminopterin at $4 \times 10^{-7} M$, thymidine at $1.6 \times 10^{-5} M$, and ouabain at $1 \times 10^{-6} M$.

Screening for hybridomas specific for Amb a I.

Culture supernatant from microtiter plate wells were screened by ELISA. Immulon 2 plates (Dynatech Laboratories, Chantilly, Va.) were coated with 50 µl of purified Amb a 1 at 1 µg/ml in PBS overnight at room temperature. Wells were then treated with blotto (5% dry nonfat milk in PBS) for 1 h and washed with PBST (PBS containing 0.05% Tween 20). Fifty µl of culture supernatant from the wells were added to the Amb a I-coated wells and incubated for 1 h. After the plates were washed with PBST, 100 µl of horseradish peroxidase-conjugated anti-human Ig (Fc) (Jackson ImmunoResearch Laboratories, West Grove, Pa.), diluted to 1/50,000 in blotto, was added to each well, and plates were incubated for 1 h. Peroxidase substrate solution containing 0.1% 3,3',5,5' tetramethyl benzidine (Sigma) and 0.003% hydrogenperoxide (Sigma) was added at 200 µl per well, and incubated at room temperature for 0.5 h. The reaction was stopped by the addition of 50 µl of 2M sulfuric acid and the OD of the reaction mixture was read with Dynatech MR 5000 at 450 nm.

First strand cDNA synthesis and polymerase chain reaction.

Total RNA was extracted from hybridoma cells using RNAzol B according to the suggested protocol (Biotecx Laboratories, Houston, Tex.). First strand cDNA was synthesized form total RNA at 42° for 1 h in a 20 µl reaction mixture containing 50 mM Tris ph 8.3, 60 mM KCl, 6 mM MgCl2, 1 mM dithiothreitol, 0.5 µg oligo (dT) 12–18 mer primer (Pharmacia, Piscataway, N.J.), 0.5 mM each of dATP, dCTP, dGTP, TIP (Pharmacia), 20 units of RNAsin RNase inhibitor (Promega, Madison, Wis.), 5 µg total RNA, and 2 units of AMV reverse transcriptase (GIBCO-BRL). Five µl of the first strand cDNA was used in a 50 µl PCR mix using the reagent kit (Perkin-Elmer Cetus, Norwalk, Conn.). The conditions were 40 cycles of denaturing at 94° for 1 min, primer annealing at 50° for 2 rain, and extension at 72° for 2 min. Primers used included 3' primer derived from the constant region and a mixture of 5' oligonucleotide primers corresponding to the leader sequence as reported by Larrick et al. (Biotechnology 7: 934 (1989)).

Anchored PCR.

Anchored PCR was carried our as described by Chen and Platsoucas (*Scand. J. Immunol.* 35: 539 (1992)). Double-stranded cDNA was prepared using the NotI-CG1 primer (5' TGCGGCCGCTGCTGAGGGAGTAGA-3') (SEQ ID NO: 1). Annealed adapters EcoRI-XmnI (5'-AATTCGAACCCCTTCG-3') (SEQ ID NO: 2) and XmnI G strand (5'-CGAAGGGGTTCG-3') (SEQ ID NO: 3) (New England Biolabs, Beverly, Mass.) were ligated to both 5' and 3' termini of the double-stranded cDNA. Adapters at the 3' end were removed by NotI digestion. The digested product was used as the template in PCR with the EcoRI-XmnI oligonucleotide as the 5' primer and CG2 (5'AGGTGTGCACGCCGCTGGTC-3') (SEQ ID NO: 4) as the 3' primer. The reaction mixture was again amplified in a second PCR with EcoRI-XmnI as the 5' primer and CG3 (5'-CAAGCTTCCACGACACCGTCACCGG-3') (SEQ ID NO: 5) as the 3' primer. DNA fragments were fractionated on 1.5% SeaPlaque low melting agarose gel (FMC Bioproducts, Rockland, Me.). The band of 500 to 650 bp was subcloned in pUC 19 and transformed into *E. Coli*. p3 cells. Colonies were hybridized with $\gamma$-$^{32}$p labeled CG4 probe (5'GCCCTGGGCTGCCTGGTCAAGGACTACTTC-3') (SEQ ID NO: 6). Positive clones with full length inserts were analyzed by DNA sequencing using a Sequenase kit (U.S. Biochemicals, Cleveland, Ohio). All four oligonucleotides, Not I-CG1, CG2, CG3 and CG4, were derived from the consensus sequences of the four human IgG subclasses and were 184, 137, 105, and 69 bp, respectively, downstream from the first bp of the CH1 domain.

Isolation of the Cα1 gene.

A human Cα1 genomic DNA clone was isolated from a WI38 genomic library (L. Yu et al. *J. Immunol.* 145: 3932 (1990)), and was mapped using various restriction enzymes. A 5.5 kb SacI/BamHI fragment containing exons encoding three constant region domains and the transmembrane anchor peptide was used to construct the expression vector.

Gene transfer by electropotation.

Linearized DNA of the Ig expression vector plasmid was introduced into NSO or Sp 2/0 cells by electroporation using the Gene Pulsar instrument (Bio-Rad, Richmond, Calif.) at 200 V and 960 µFd. Transfected cells were selected in Iscove's modified Dulbecco's medium (GIBCO) containing 2% FCS, G418 (GIBCO) at 0.2 mg/ml for the K-chain plasmid uptake and mycophenolic acid (Sigma) at 0.2 ug/ml, xanthine (Sigma) at 50 ug/ml for the H-chain plasmid uptake. The frequency of tranfectants resistant to both selections was approximately $5\times10^{-5}$.

Quantitation of IgA and IgG production.

Stable drug-resistant transfectants were screened for the production of human IgA or IgG by ELISA. Immulon 2 plates were coated with goat anti-human κ antibodies (Fisher Scientific, Orangeburg, N.Y.) at 1 µg/ml in PBS overnight at room temperature, and then blocked with blotto for 1 h. After the wells were washed with PBST, 50 µl of culture supernatant was added to each well and the plate was incubated for 1 h. After the wells were washed, peroxidase-labeled goat anti-human IgA (Kirkegaard & Perry Laboratories, Gaithersburg, Md.) at 1 to 10,000 dilution or peroxidase-labeled goat anti-human IgG (Fc) (Jackson Laboratories) at 1 to 50,000 dilution was added for detection of IgA or IgG, respectively. Peroxidase substrate was then added as described above.

Antibody purification and analyses.

Protein A column (Repligen, Cambridge, Mass.) was used to purify IgG from culture supernatant of transfectoma cells according to manufacturer's protocol. For purifying IgA, anti-human IgA1 mAb 55-5-1 was coupled to Tresyl-activated agarose (Schliecher & Shuell, Keene, N. H.) according to the manufacturer's suggested procedure. After culture supernatant was passed through the column, the column was extensively washed with PBS, and bound IgA was eluted with 50 mM diethylamine, pH 11.5. IgA and IgG was dialyzed against PBS and concentrated using Centiprep concentrators (Amicon, Danvers, Mass). Antibody samples were analyzed by SDS-PAGE on 4% gels under nonreducing and 12% gels under reducing conditions in phosphate buffer. Protein was also transferred to nitrocelluose by using a Bio-Rad Trans-Blot SD Semi-Dry Electrophoretic Transfer Cell apparatus at 15 V for 0.5 h. The nitrocellulose filters were treated with blotto for 0.5 h and then with peroxidase-labeled goat anti-human kappa at 1 to 5,000 dilution. After three washes in PBST, the filters were developed by incubation in TMB substrate solution (Kirkegaard & Perry Laboratories) at room temperature.

Amb a I binding assay

Wells of Immulon 2 plates were coated with 100 µl of purified Amb a I at 1 µg/ml in PBS overnight at room temperature, blocked with blotto for 1 h, and washed with PBST. One hundred µl of purified IgA or IgG at different concentration was added to each well, and incubated for 1 h. After the wells were washed with PBST, 100 µl of alkaline phosphatase-conjugated anti human kappa (Southern Biotechnology Associates, Birmingham, Ala.) at 1 to 1000 dilution was added. After 1 h, the webs were washed with PBST and alkaline phosphatase substrate at 1 mg/ml (Bio-Rad) was added. After 30 minutes at 37°, 100 µl of 5% EDTA was added to stop the reaction mixture was read with a Dynatech MR 5000 at 410 nm.

The purified recombinant human IgG and IgA monoclonal antibodies were shown to bind to the Amb a I by ELISA. The concentration needed to achieve 50% of the maximum binding was determined to be approximately 0.5 µg/ml for the recombinant IgG and IgA, as compared to 0.7 µg/ml for the hybridoma-derived Amb a I-binding IgA. Since the hybridoma-derived IgG was available only in the partially purified form, its concentration was estimated by ELISA. This may have resulted in the Amb a I binding difference observed for the partially purified hybridoma-derived IgG and the purified recombinant IgG and IgA.

It should be understood that the terms, expressions, and examples herein are exemplary only and not limiting, and those skilled in the art will recognize, or be able to ascertain using no more than routine experimentation, many equivalents to the specific embodiments of the invention described herein. All such equivalents are intended to be encompassed by the following claims.

What is claimed is:

1. Allergen-specific human IgA monoclonal antibodies specific for allergens associated with IgE-mediated allergic reactions.

2. A monoclonal antibody of claim 1, in which the allergen is Amb a I, Der p I, Der f I, Can f I, or Fel d I.

* * * * *

UNITED STATES PATENT AND TRADEMARK OFFICE
CERTIFICATE OF CORRECTION

PATENT NO. : 5,670,626
DATED : September 23, 1997
INVENTOR(S) : Tse Wen Chang

It is certified that error appears in the above-identified patent and that said Letters Patent is hereby corrected as shown below:

Col. 1, line 35, after "bronchial tracts", please insert -- (in patients with allergic asthma), and the mucosal surfaces of the conjunctiva of the eyes--;
Col. 1, line 65, "haft" should be -- half --;
Col. 3, line 42, "TMs" should be --This--;
Col. 3, line 66, "altergens" should be -- allergens --;
Col. 4, line 41, "altergens" should be -- allergens --;
Col. 7, line 9, "SF2/0" should be -- SP2/0 --;
Col. 7, line 60, delete the word "a" at the end of the line;
Col. 9, last line, "6" should be superscripted (moved up to the height of the preceding "-" sign);
Col. 10, line 29, change "TIP" to -- TTP --;
Col. 10, line 35, change "rain" to -- min --;
Col. 10, line 62, the word "probe" should not have spaces between the letters.

Signed and Sealed this

Tenth Day of February, 1998

*Attest:*

*Attesting Officer*

BRUCE LEHMAN

*Commissioner of Patents and Trademarks*